United States Patent
Kuhn et al.

(10) Patent No.: US 10,232,189 B2
(45) Date of Patent: Mar. 19, 2019

(54) GUIDED PHOTODYNAMIC THERAPY

(71) Applicant: KONINKLIJKE PHILIPS N.V., Eindhoven (NL)

(72) Inventors: Michael Harald Kuhn, Hamburg (DE); Christine Charlotte Jutta Muzel, Eindhoven (NL); Bernardus Hendrikus Wilhelmus Hendriks, Eindhoven (NL); Gerardus Wilhelmus Lucassen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 129 days.

(21) Appl. No.: 14/384,278

(22) PCT Filed: Mar. 26, 2013

(86) PCT No.: PCT/IB2013/052385
§ 371 (c)(1),
(2) Date: Sep. 10, 2014

(87) PCT Pub. No.: WO2013/144830
PCT Pub. Date: Oct. 3, 2013

(65) Prior Publication Data
US 2015/0057724 A1 Feb. 26, 2015

Related U.S. Application Data

(60) Provisional application No. 61/615,935, filed on Mar. 27, 2012.

(51) Int. Cl.
*A61N 5/06* (2006.01)
*G06F 19/00* (2018.01)
(Continued)

(52) U.S. Cl.
CPC .............. *A61N 5/062* (2013.01); *A61B 90/37* (2016.02); *G06F 19/00* (2013.01); *G16H 50/50* (2018.01);
(Continued)

(58) Field of Classification Search
CPC ............ A61N 5/062; A61N 2005/0628; A61N 2005/063; A61N 5/0603;
(Continued)

(56) References Cited

U.S. PATENT DOCUMENTS 6,471,710 B1 * 10/2002 Bucholtz .............. G01B 11/005
600/229
6,614,972 B1 * 9/2003 Lundin ................ G02B 6/0005
385/115
(Continued)

FOREIGN PATENT DOCUMENTS

CN 102081415 A 6/2011
JP 2010500140 A 1/2010
(Continued)

OTHER PUBLICATIONS

Merriam-Webster, definition of "bundle", accessed Aug. 2, 2016, http://www.merriam-webster.com/dictionary/bundle.*
(Continued)

*Primary Examiner* — Lynsey Eiseman
*Assistant Examiner* — Jonathan Kuo

(57) ABSTRACT

A photodynamic therapy (PDT) system includes an elongated interventional device with a bundle of optical fibers forming respective light exit ports which can be individually accessed. The bundle has an optical shape sensing fiber arranged for sensing position and orientation of the light exit ports. A processor is configured to generate a light dose signal to allow generation of light outputs to the optical fibers. The light dose signal is generated in response to the
(Continued)

determined position and orientation of the light exit ports, and three-dimensional body anatomy image information obtained by a first image modality. The processor is also configured to take image information regarding distribution of a photo sensitizer in the body tissue as input, as well as take into account image information regarding a concentration of oxygen in the body tissue.

19 Claims, 4 Drawing Sheets

(51) Int. Cl.
*G16H 50/50* (2018.01)
*A61B 90/00* (2016.01)
*A61B 34/20* (2016.01)
*G02B 6/26* (2006.01)
*G02B 6/04* (2006.01)
*G02B 6/02* (2006.01)

(52) U.S. Cl.
CPC ..... *A61B 2034/2061* (2016.02); *A61N 5/0603* (2013.01); *A61N 2005/063* (2013.01); *A61N 2005/0628* (2013.01); *G02B 6/02057* (2013.01); *G02B 6/04* (2013.01); *G02B 6/262* (2013.01)

(58) Field of Classification Search
CPC ........ A61N 5/06–2005/073; A61B 2034/2061; A61B 19/5225; A61B 90/37; A61B 18/20–18/28; G02B 6/02057; G02B 6/04; G02B 6/262
USPC ..................................... 607/88–95; 606/1–19
See application file for complete search history.

(56) References Cited

U.S. PATENT DOCUMENTS

| | | | | |
|---|---|---|---|---|
| 6,869,430 | B2* | 3/2005 | Balbierz | A61B 18/1206 606/41 |
| 7,813,599 | B2* | 10/2010 | Moore | G01B 11/18 385/12 |
| 2007/0282404 | A1 | 12/2007 | Cottrell et al. | |
| 2010/0099951 | A1* | 4/2010 | Laby | A61B 1/0052 600/144 |
| 2011/0098533 | A1* | 4/2011 | Onoda | A61B 1/0051 600/117 |
| 2011/0295347 | A1* | 12/2011 | Wells | A61N 1/36032 607/89 |
| 2012/0022510 | A1* | 1/2012 | Welches | A61B 18/22 606/3 |
| 2014/0005465 | A1* | 1/2014 | Ribbing | A61N 5/103 600/3 |

FOREIGN PATENT DOCUMENTS

| | | |
|---|---|---|
| JP | 2011030735 A | 2/2011 |
| JP | 2011167344 A | 9/2011 |
| WO | 0113060 A1 | 2/2001 |
| WO | 2008020050 A1 | 2/2008 |
| WO | 2008062000 A1 | 5/2008 |
| WO | 2010089416 A1 | 8/2010 |
| WO | 2011080606 A1 | 7/2011 |
| WO | 2011086432 A2 | 7/2011 |
| WO | 2011098926 A1 | 8/2011 |

OTHER PUBLICATIONS

E.M.C. Keijzer, "Light transport for medical laser treatments", PhD Thesis, Technical University Delft, Dec. 6, 1993, pp. 1-207.

Thomas J. Farrell et al, "A diffusion theory model of spatially resolved, steady-state diffuse reflectance for the noninvasive determination of tissue optical properties in vivo", Med. Phys. vol. 19, No. 4, Jul./Aug. 1992, pp. 879-888.

Chenglin Li et al, "Fully distributed chirped FBG sensor and application in laser-induced interstitial thermotherapy", IEEE Xplore, Abstract.

* cited by examiner

GUIDED PHOTODYNAMIC THERAPY

CROSS-REFERENCE TO PRIOR APPLICATIONS

This application is the U.S. National Phase application under 35 U.S.C. § 371 of International Application Serial No. PCT/IB2013/052385, filed on Mar. 26, 2013, which claims the benefit of U.S. Application Ser. No. 61/615,935, filed on Mar. 27, 2012. These applications are hereby incorporated by reference herein.

FIELD OF THE INVENTION

The present invention relates to the field of medical devices or equipment. More specifically, the invention relates to medical equipment for and a method for photodynamic treatment.

BACKGROUND OF THE INVENTION

Photodynamic therapy (PDT) treats tumors by a combination of photosensitizer molecules that are preferentially taken up by the tumor cells and illumination with light. The light excites the photosensitizer molecules to become active radicals through the formation of negatively charged singlet oxygen that kills the tumor cells. PDT is a very attractive therapy since it leaves connective tissue intact, while destroying tumor cells.

With PDT it is difficult to control and measure the concentration of the photosensitizer drug in the tissue. The toxic reaction needs the drug, oxygen (tumors are often hypoxic) and light. For providing the drug, there are concepts of oral, intravenous and topical administration (injection into the tumor). A problem with PDT is that it is difficult to administer the required light dose in a proper fashion. Too little light will save connective tissue, but also leave tumor cells unaffected, while too much light will lead to damage of connective tissue.

For example PDT is of utmost importance for treatment of prostate cancer, as this disease remains indolent for long times but can exhibit lesions that turn aggressive and need to be destroyed—which calls for a repeatable therapy. In contrast, external beam (photon and Ion) therapy and brachytherapy leave irreversible permanent damage behind in all tissue, and render tissue boundaries invisible, which is a problem for surgeons in case subsequent surgical resection is planned. PDT can also advantageously be applied for treatment of cancer in the mouth, esophagus, lung, and cervix. It may also be used for treatment of breast cancer.

WO 2008/062000 A1 discloses a PDT treatment method, where measurements of treatment parameters are done prior to the treatment and updated after a treatment step. Thus, the method suffers from poor control of the light administering during treatment.

SUMMARY OF THE INVENTION

It would be advantageous to provide a PDT system and method capable of precisely controlling light dose administering during treatment.

In a first aspect, the invention provides a PDT system comprising
an interventional device comprising a bundle of a plurality of optical fibers with distributed fibers ends forming respective light exit ports arranged to emit light in different directions, wherein the bundle comprises an optical shape sensing fiber arranged for sensing position and orientation of the fiber ends,
an optical console arranged for connection to the plurality of optical fibers, and to generate individually controllable light outputs to the plurality of optical fibers in response to a light dose signal,
a position console arranged for connection to the optical shape sensing fiber and to determine position and orientation of the fiber ends of the interventional device, based on an optical measurement applied to the optical shape sensing fiber, and
a processor arranged to execute a control algorithm so as to generate the light dose signal to allow the optical console to generate light outputs to the plurality of optical fibers accordingly, wherein the control algorithm generates the light dose signal in response to:
position and orientation of the fiber ends from the position console, and
three-dimensional body anatomy image information obtained by a first image modality capable of discriminating between different anatomical tissues inside a body.

Such PDT system advantageous, since it allows precise administering of light for PDT treatment in a target volume, e.g. a tumor, where the interventional device has been inserted. The system allows the control algorithm to determine the optimal light distribution pattern based on the actual position of the light exit ports of the interventional device, when present in the body, preferably in the tumor, by applying a pattern of light intensities to the individual optical fibers. The optical shape sensing fiber, e.g. using Fiber Bragg Gratings, allows precise three-dimensional tracking of position and orientation since bending of the fiber optical shape sensing fiber as well as rotation around its longitudinal axis can be determined, as known in the art. Light application fibers and position tracking sensor can be integrated into one single elongated interventional device. Taking into account the actual position and orientation of the light exit ports and the shape of the tumor which can be identified in the three-dimensional body anatomy image information (obtained during PDT treatment by real-time imaging or obtained before the PDT treatment), it is possible for the control algorithm e.g. by applying light diffusing models, to determine a resulting light pattern from the interventional device which will result in the most efficient PDT treatment of the tumor, while saving as much as possible of the connective tissue. E.g. this can be obtained by first determining the optimal light dose distribution for the best possible PDT effect, and then determining a light dose signal with individual light intensity values for each of the plurality of optical fibers, so as to provide a resulting light dose distribution from the interventional device which is as close to the optimal light dose distribution as possible.

In some embodiments, the control algorithm is arranged to determine a more preferred position and orientation of the interventional device, if calculations indicate that such position and orientation can be obtained where a better coverage of light in the tumor, and possibly also save more of the connective tissue. Hereby, the operator can change the position and orientation of the interventional device accordingly before the PDT treatment is performed.

The PDT system is applicable within a number of medical applications, a non-exhaustive list of diseases are: prostate cancer, and cancer in the mouth, esophagus, lung, and cervix. It may also be used for treatment of breast cancer. All of these applications will benefit from the precise light dose administering which can be achieved with the system according to the first aspect, where effective tumor treatment can be combined with saving of connective tissue.

In preferred embodiments, the control algorithm is arranged to generate a light dose signal with individual light intensity information for each of the plurality of optical fibers so as to obtain a spatial light pattern from the interventional device which matches a target volume identified in the three-dimensional body anatomy image, based on the position and orientation of the fiber ends, and based on knowledge about light emission direction patterns for the plurality of fiber ends. A desired light intensity distribution in the tissue, e.g. the tumor, is generated by controlling intensities of a mix of the light contributions from each of the optical fiber ends. E.g. a bundle of two or more, more preferably a bundle of 5 or more, more preferably 10 or more, such as 10-30, or possibly even more optical fibers can be used, so as to allow a detailed three-dimensional light distribution pattern, thus allowing a good match to a given tumor shape.

In one embodiment, the bundle of optical fibers is designed to produce a non-rotational symmetric light distribution, thus allowing a more optimal distribution of light by rotation of the interventional device.

The control algorithm preferably comprises applying a light diffusion modelling, e.g. taking into account body tissue.

The first image modality can be such as: X-ray, Magnetic Resonance Imaging (MRI), Computed Tomography (CT), ultrasound, or Positron Emission Tomography-Computed Tomography (PET-CT). However, other modalities can be used, as long as it is possible to distinguish the target volume, e.g. the tumor, from the connective tissue.

The control algorithm may be arranged to generate the light dose signal in response to image information obtained by a second image modality, regarding distribution of a photosensitizer in the body tissue. The second image modality can be such as: MR spectroscopy, $^{19}F$ Magnetic Resonance Imaging (MRI), nuclear Positron Emission Tomography (PET) imaging, nuclear Single Photon Emission Computed Tomography (SPECT) imaging, and magnetic particle imaging. With this additional input, the control algorithm can take into account an uneven distribution of the photosensitizer which has been administered, and design the optimal light dose distribution for the best possible PDT effect accordingly.

The control algorithm may be arranged to generate the light dose signal in response to image information obtained by a third image modality, regarding a concentration of oxygen in the body tissue. The third image modality may be such as: FluoroMISOnidazole Positron Emission Tomography (FMISO-PET) or Magnetic Resonance Imaging (MRI). With this additional input, the control algorithm can take into account an actual distribution of oxygen level in the tumor and connective tissue, which affects the PDT efficiency. Thus, the control algorithm has yet another input which allow a refinement of designing the optimal light dose distribution for the best possible PDT effect accordingly.

As already addressed, in some embodiments, the control algorithm may be arranged to determine a planned position of the interventional device in relation to an identified target volume, based on an actually achieved position of the fiber ends and the three-dimensional body anatomy image information. Thus, in case it can be predicted that a changed position or orientation of the interventional device can provide a better light distribution, the control algorithm can determine such position and orientation and provide an output to the operator accordingly.

In some embodiments, the control algorithm comprises applying a dynamic light tissue model for calculating a light distribution as a function of temperature dependent local optical properties, photosensitizer concentration, and oxygen concentration in the body tissue. By providing such a dynamic model which is preferably updated in real-time, the design of the optimal light does distribution can be further refined. Especially, the dynamic light tissue model may comprise updating at each time step one or more of:
1) a static light distribution based on actual optical properties, and resulting toxicity based on photosensitizer and oxygen concentration,
2) a heat diffusion calculation based on a light diffusion calculation,
3) a damage integral calculation,
4) a change in optical properties due to a change in temperature,
5) a change in photosensitizer concentration, and
6) a change in oxygen concentration.

In a special embodiment, all of 1)-6) are updated for each time step.

In preferred embodiments, the optical shape sensing fiber comprises Fiber optic Bragg Gratings (FBGs), so as to allow the position console to track a three-dimensional shape of the bundle of optical fibers, and to determine the position and orientation of the fiber ends accordingly. Such use of FBGs and the application of suitable optical measurement signals is known. In the present application it is understood that the optical shape sensing fiber or fibers, is/are preferably placed such in relation to the optical fibers, that the optical shape sensing fiber(s) bend and rotate around a longitudinal axis together with the bundle of optical fibers. Hereby, a good match is obtained between the sensed position and orientation and the actual position and orientation of the light exit ports. E.g. the optical shape sensing fiber(s) can be centrally arranged with the plurality of optical fibers symmetrically or non-symmetrically arranged around the optical shape sensing fiber(s).

In some embodiments, the interventional device comprises a light intensity sensor. This allows an input to the control algorithm of actual light intensity during treatment, e.g. allowing use of one or more associated light applying devices. Especially, the control algorithm may be arranged to generate the light dose signal in response to information received from the light intensity sensor, so as to adapt light distribution from the interventional device to light applied by an associated additional light source.

In some embodiments, the optical console is arranged to tune a wavelength of the light to the optical fibers, and/or multiple wavelength can be used which provide different penetration depths into the tissue, so that an improved illumination of the photosensitizer can be obtained.

It is to be understood that the type of light used for the PDT treatment and the type of photosensitizer used is such as known in the art.

The control algorithm can be implemented as a software program arranged for execution on a suitable processor system or computer.

The size and shape of the interventional device, such as thickness and number of the optical fibers, is understood to be selected for a given application.

In a second aspect, the invention provides a PDT treatment method comprising
providing in a body an interventional device comprising
a bundle of a plurality of optical fibers with distributed fibers ends forming respective light exit ports arranged to emit light in different directions, and an optical shape sensing fiber arranged for sensing position and orientation of the fiber ends, determining position and orientation of the fiber ends by applying an optical measurement to the optical shape sensing fiber, providing a three-dimensional body anatomy image information obtained by a first image modality capable of discriminating between different anatomical tissues inside the body, and generating individually light outputs to the plurality of optical fibers in response to the position and orientation of the fiber ends and the three-dimensional body anatomy image information.

It is appreciated that the same advantages and embodiments of the first aspect apply as well for the second aspect. In general the first and second aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
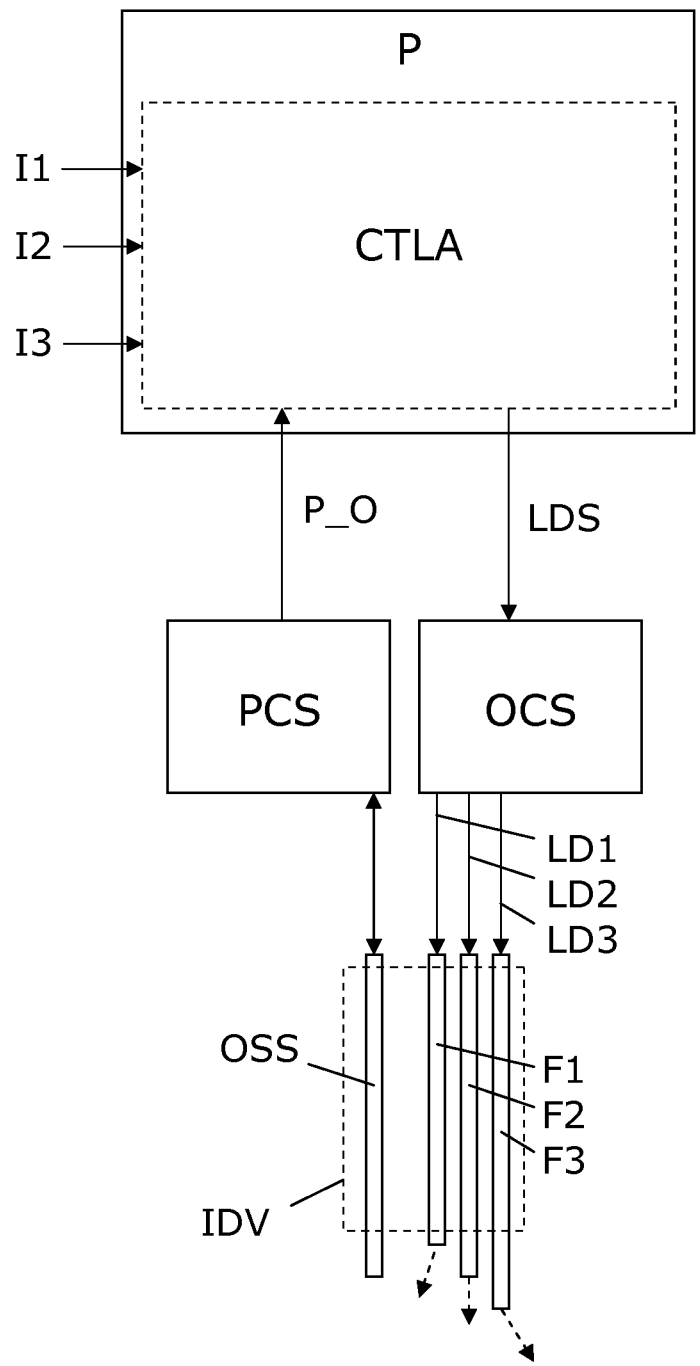
FIG. 1 shows a block diagram of an embodiment of the PDT system of the invention.

FIG. 1 illustrates a simple block diagram of a PDT system embodiment according to the invention. An interventional device IDV in the form of an elongated needle, catheter, endoscope or the like, is arranged for insertion into the body, e.g. a tumor, of a patient to be treated with PDT. The interventional device IDV includes a bundle of optical fibers F1-F3 which are individually accessible in one end, and in the opposite end they have fiber ends which serve as light exit ports. The optical fibers F1-F3 are spatially distributed and with fiber ends serving to distribute light in different directions (indicated by dashed arrows) which allows a mix of light from the fiber ends to generate a resulting complex light distribution. For illustration, only 3 fibers F1-F3 are shown, but in practical applications any number of two or more can be used, e.g. 5-10, 10-30, or even more fibers can be used, so as to allow generation of a complex light distribution suited to provide light to a complex tumor shape.

One or ore optical shape sensing fibers OSS, preferably based on Fiber Bragg Gratings, is/are also integrated in the interventional device IDV. In a manner known from other applications, a position console PCS is connected with the optical shape sensing fiber(s) OSS so as to determine bending and rotation around its longitudinal axis. Hereby, since the OSS is structurally linked with the optical fibers F1-F3, the position and orientation of the light exit ports of the optical fibers F1-F3 can be determined. Thus, the actual 3-D position and orientation of the light exit ports can be determined in the position console PCS and be applied to a processor P in the form of a position and orientation signal P_O.

The processor P, e.g. a general computer or a dedicated processor system, executes a control algorithm CTLA in the form of a light dose planning software which takes the position and orientation signal P_O as input. In the illustrated embodiment, the control algorithm CTLA further takes as input:

Three-dimensional body anatomy image information I1 obtained by a first image modality, e.g., capable of discriminating between different anatomical tissues inside a body. Thus, this image I1 preferably includes information allowing identification of the shape of the tumor, i.e. the target volume for the light application for the PDT treatment. The first image modality can be: X-ray, MRI, CT, ultrasound, and PET-CT. Known image processing methods exist to reliably delineate a tumor based on such image information I1.

Image information I2 obtained by a second image modality, regarding distribution of a photosensitizes in the body tissue. This distribution influences the optimal light dose, and thus important for providing the light dose distribution. The second image modality can be: MR spectroscopy, $^{19}$F MRI, nuclear PET imaging, nuclear SPECT imaging, and magnetic particle imaging.

Image information I3 obtained by a third image modality, regarding a concentration of oxygen in the body tissue. The oxygen in the tissue under PDT treatment also influences the optimal light to be applied, and is thus important for the control algorithm CTLA to take into account in designing the light dose distribution to be applied. The third image modality can be such as: FMISO-PET and MRI.

Based on the described inputs I1, I2, I3, P_O the control algorithm CTLA applies various light diffusion models involving estimated optical parameters for the various types of tissue in the PDT treatment area. In response, the control algorithm CTLA generates a light distribution pattern in the form of a light distribution signal LDS to an optical console OCS which generates in response, individual light intensities LD1, LD2, LD2 to the respective optical fibers F1, F2, F3 which then generate a resulting light distribution pattern from the tip of the interventional device IDV. With the inputs I1, I2, I3 combined with the precise knowledge of the light exit ports of the interventional device IDV, it is possible to apply light which matches the planned light pattern for optimal PDT treatment of a tumor with a given shape and size, while saving connective tissue.

To determine the optical light output for each fiber F1, F2, F3 the function of the control algorithm CTLA in one embodiment is as follows. The shape of the tumor is known from the three-dimensional body anatomy image information I1. The position P_O of the fiber ends are known from the position console PCS. Making use of Monte Carlo (MC) modeling of light diffusion in and around the tumor tissue (the optical parameters light absorption and scattering as a function of wavelength are known from for instance a look-up-table), it is possible to calculate what the intensity of the light output of the fiber ends must be in order to have at all location in the tumor the required optical intensity for PDT treatment, taking into account knowledge of tissue heterogeneity inside the tumor, tissue oxygenation and/or the local photosensitizer distribution, if such information is available, e.g. by suitable imaging approaches. A forward MC calculation yields the deposited energy and light distribution as a function of the optical properties and positions in the tissue at a given input light distribution, and the toxicity created by the interaction of this light distribution with oxygen and photosensitizer distributions can be computed. The required light distribution can then be determined by altering the input light distribution in such a way to match the local tissue light distribution and toxicity to the required light distribution and toxicity.

Information about light diffusion models can be found in: T. J. Farrell and M. S Patterson and B. Wilson, "A diffusion theory model of spatially resolved, steady-state diffuse reflectance for noninvasive determination of tissue optical properties in vivo", Med. Phys. 19 (1992) p 879, and E. M. C. Keijzer, "Light transport for medical laser treatments", PhD Thesis Technical University Delft, 1993.

During the PDT treatment the light distribution changes due to the varying optical properties, temperature and the toxicity changes with the available oxygen and photosensitizer distribution. This requires a dynamic model to maintain optimal light treatment. Thus, in some embodiments, the control algorithm CTLA is arranged to provide such dynamic update of calculations for each time step. In a specific embodiment of such dynamic update, in each time step the following updates are done:
1. Static light distribution based on actual optical properties, and resulting toxicity based on photosensitizer and oxygen concentration.
2. Heat diffusion step using the deposited energy and light distribution from the MC calculation as input.
3. Damage integral calculation using the Arrhenius constant.
4. Change in optical properties due to changed temperature.
5. Change in photosensitizer concentration,
6. Change in oxygen concentration.
7. Make a time step repeat from 1.

Figure 2:
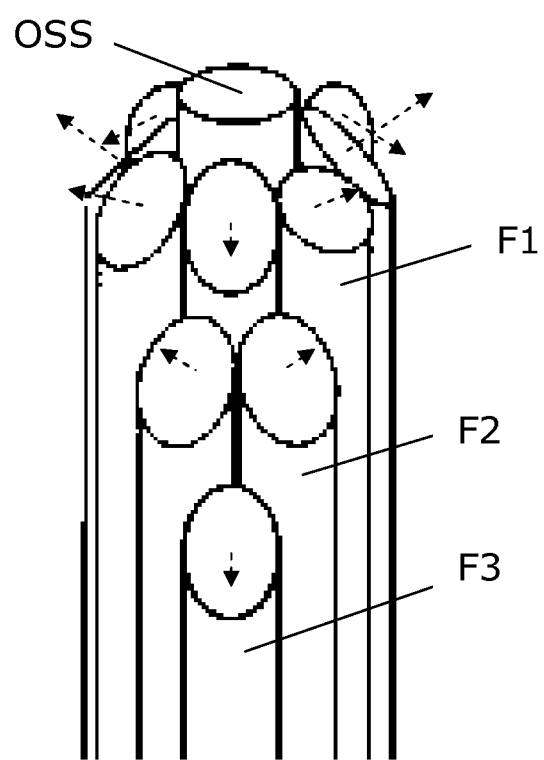
FIG. 2 illustrates a 3-D view of a tip of an interventional device embodiment.

FIG. 2 illustrates a 3-D view of a tip of an interventional device embodiment. A bundle of optical fibers F1, F2, F3 (10 single fibers are visible) deliver light from their fiber ends. The fiber ends are angled so as to emit light in different direction (illustrated by dashed arrows). The optical fibers F1, F2, F3 are placed around a central optical shape sensing fiber OSS in several layers or rings. The optical fibers F1, F2, F3 are placed with their fiber ends and thus their light exit port at different spots in all directions along a certain length at the bundle tip. The light delivering fibres may have angulated output surfaces.

In the end opposite the tip end, the optical fibers F1, F2, F3 are individually accessible, and thus individual light intensities can be applied to the optical fibers F1, F2, F3. Thus, the light application are effectively variable light sources at the end of each fibre, which allows dynamically producing a 3-D light dose volume when the tip of the interventional device is inserted in a tumor, making use also of the rotational degree of freedom as well as axial position of the fiber ends. In addition to the intensity, the wavelength of the light in each fibre F1, F2, F3 can be varied, such as to influence its wavelength-dependent penetration into the tissue—provided the phototoxicity can be achieved with a range of wavelengths.

The function of the optical shape sensing fiber OSS, preferably by the use of Fiber Bragg Gratings, is explained below.

Figure 3A:
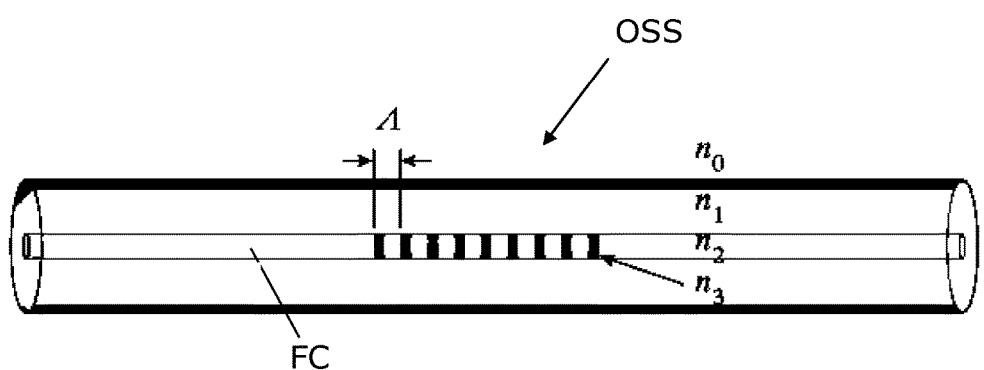
FIG. 3a-c illustrate the function of the FBGs.
Figure 3B:
Figure 3C:
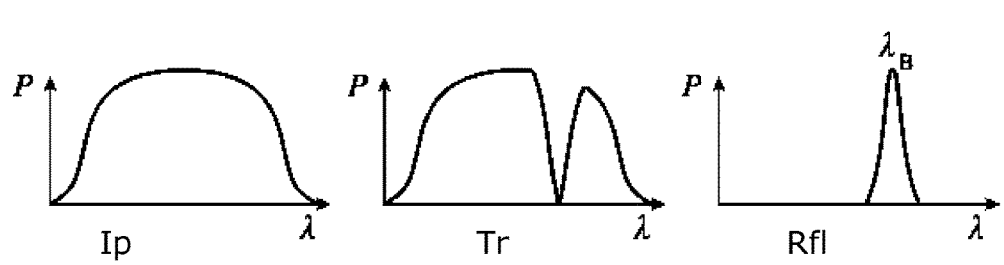

FIG. 3a-c serve to illustrate the use of Fiber Bragg Gratings (FBGs) in an optical shape sensing fiber OSS which can be used to track the three-dimensional shapes of an interventional device in real-time. It is known from prior art that three or more fibers with integrated FBGs can be utilized together to track the 3-D shapes of the fibers in real-time.

FBGs are short segments of optical fiber that reflect particular wavelengths of light and transmits all others. This is achieved by adding a periodic variation of the refractive index in the fiber core, which generates a wavelength-specific dielectric mirror. An FBG can therefore be used as an inline optical filter to block certain wavelengths, or as a wavelength-specific reflector.

The fundamental principle behind the operation of an FBG is Fresnel reflection at each of the interfaces where the refractive index is changing. For some wavelengths the reflected light of the various periods is in phase with one another so that constructive interference exists for reflection and consequently, destructive interference for transmission.

FIG. 3a illustrates an optical shape sensing fiber OSS with a fiber core FC inside a fiber with another refractive index n1. The refractive index of the fiber core FC changes along its length, namely between n2 and n3, as indicated with black and white color, and which is also indicated in the graph of FIG. 3b, showing the core refractive index along the core. In FIG. 3c a spectral response is shown for a broadband input signal Ip, being split into transmitted Tr and reflected Rfl components in the fiber core. The three graphs show power P versus signal wavelength λ. As seen, in the transmitted spectrum Tr, a dip at a characteristic wavelength is observed, while in the reflected spectrum, the opposite effect is seen, i.e. a peak around the characteristic wavelength $\lambda_B$.

The Bragg wavelength is sensitive to strain as well as to temperature. This means that Bragg gratings can be used as sensing elements in fiber optical sensors. In a FBG sensor, the measurand causes a shift in the Bragg wavelength, $\Delta\lambda_B$. The relative shift in the Bragg wavelength, $\Delta\lambda_B/\lambda_B$, due to an applied strain ($\varepsilon$) and a change in temperature ($\Delta T$) is approximately given by:

$$\frac{\delta\lambda_B}{\lambda_B} = C_s\varepsilon + C_T\Delta T$$

The coefficient Cs is called the coefficient of strain and its magnitude is usually around $0.8\times10^{-6}/\mu\varepsilon$ (or in absolute quantities about 1 pm/K). The coefficient CT describes the temperature sensitivity of the sensor; it is made up of the thermal expansion coefficient and the thermo optic effect. Its value is around $7\times10^{-6}/K$ (or as an absolute quantity 13 pm/K).

Figure 4:
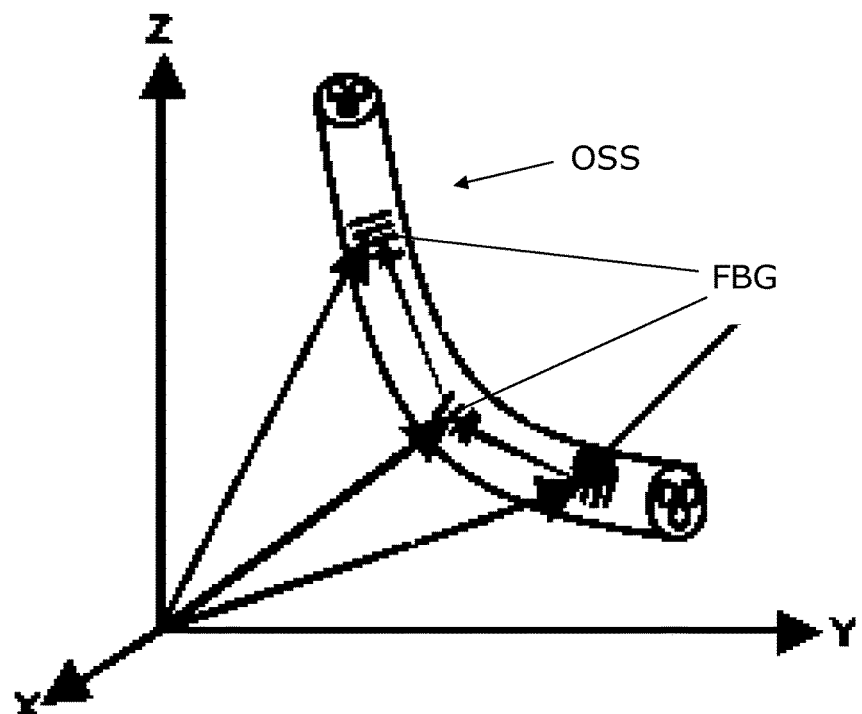
FIG. 4 illustrates a structure with 3 fiber cores and distributed FBGs.

FIG. 4 shows an illustration of an optical shape sensing fiber OSS in the form of a structure with 3 fiber cores and distributed FBG sensors in a 3-D coordinate system with axes Y, Y, Z. One of the main advantages of the technique is that various sensor elements can be distributed over the length of a fiber. Incorporating 3 cores with various sensors (gauges) along the length of a fiber that is embedded in a structure allows for the 3 dimensional form of such a structure to be precisely determined. Along the length of the fiber, at various positions, 3 FBG sensors are located. From the strain measurement of each FBG the curvature of the structure can be inferred at that position. From the multitude of measured positions, the total 3 dimensional form is determined. From this, it is possible to determine both position and orientation of the light exit ports of an interventional device with high precision.

Figure 5:
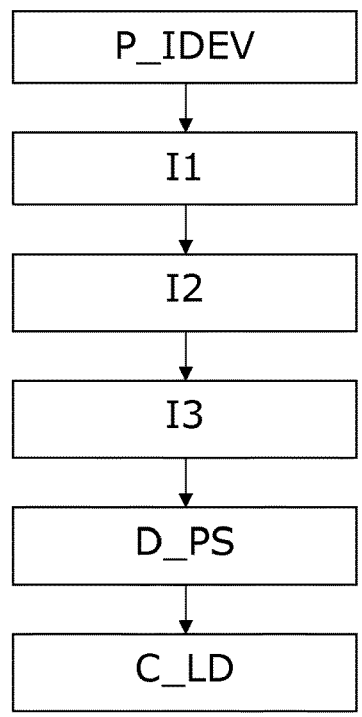
FIG. 5 illustrates steps of a PDT method embodiment.

FIG. 5 shows a block diagram of a PDT method embodiment. It is to be understood that the various steps can be performed in different order.

In a first step P_IDEV, an interventional device is provided and inserted in the body tissue, e.g. a tumor. The interventional device comprises a bundle of a plurality of optical fibers with distributed fibers ends forming respective light exit ports arranged to emit light in different directions, and an optical shape sensing fiber arranged for sensing position and orientation of the fiber ends.

Next, a three-dimensional body anatomy image information is provided I1 by a first image modality, thus allowing determination of size and shape of a tumor for PDT treatment. Next, image information regarding distribution of a photosensitizer in the body tissue is provided I2 by a second image modality. Next, image information regarding a concentration of oxygen in the body tissue is provided I3 by a third image modality.

Position and orientation is determined D_PS of the fiber ends and thus the light exit ports is obtained by applying an optical measurement to the optical shape sensing fiber.

Finally, a light distribution pattern is calculated C_LD, and individually light outputs to the plurality of optical fibers are generated in response to the position and orientation of the fiber ends and the three-dimensional body anatomy image information.

To sum up, the invention provides a Photodynamic Therapy (PDT) system with an elongated interventional device (IDV) with a bundle of optical fibers (F1, F2, F3) forming respective light exit ports which can be individually accessed. The bundle has an optical shape sensing fiber (OSS), e.g. including Fiber Bragg Gratings, arranged for sensing position and orientation (P_O) of the light exit ports. A processor executes a control algorithm which generate a light dose signal (LDS) to allow generation of light outputs (LD1, LD2, LD3) to the plurality of optical fibers (F1, F2, F3) accordingly. The control algorithm generates the light dose signal (LDS) in response to the determined position and orientation of the light exit ports (P_O), and three-dimensional body anatomy image information obtained by a first image modality (I1), e.g. X-ray, MRI, CT, ultrasound, or PET-CT. This combination allows precise application of a light dose distribution for PDT treatment of a tumor with a minimal destruction of connective tissue. In embodiments, the control algorithm takes image information regarding distribution of a photosensitizer in the body tissue (I2) as input. The control algorithm may further take into account image information regarding a concentration of oxygen in the body tissue (I3). Both of such inputs allow a more precise PDT light application.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A photodynamic treatment system comprising:
   an interventional device comprising a bundle of a plurality of optical fibers with distributed fiber ends forming respective light exit ports arranged to emit light in different directions, wherein the bundle comprises an optical shape sensing fiber shared by the plurality of optical fibers for determining actual position and orientation of the fiber ends actually achieved during use;
   an optical console arranged for connection to the plurality of optical fibers, and configured to generate individually controllable light outputs to the plurality of optical fibers in response to a light dose signal;
   a position console arranged for connection to the optical shape sensing fiber and configured to determine the actual position and orientation of the fiber ends of the interventional device based on an optical measurement applied to the optical shape sensing fiber; and
   a processor configured to generate the light dose signal to allow the optical console to generate the individually controllable light outputs to the plurality of optical fibers,
   wherein the processor is configured to determine and generate the light dose signal in response to:
   the actual position and orientation of the fiber ends received from the position console and determined from the optical shape sensing fiber,
   knowledge about light emission direction patterns of the light emitted in the different directions from the respective light exit port of the plurality of fiber ends,
   a three-dimensional body anatomy image obtained by a first image modality configured to discriminate between different anatomical tissues inside a body, and
   image information obtained by a second image modality regarding a concentration of oxygen in the body tissue.

2. The photodynamic treatment system according to claim 1, wherein the processor is configured to generate the light dose signal with individual light intensity information for each of the plurality of optical fibers so as to obtain a spatial light pattern from the interventional device which matches a target volume identified in the three-dimensional body anatomy image.

3. The photodynamic treatment system according to claim 1, wherein the processor is configured to apply a light diffusion modelling.

4. The photodynamic treatment system according to claim 1, wherein the first image modality is selected from: X-ray, MRI, CT, ultrasound, and PET-CT.

5. The photodynamic treatment system according to claim 1, wherein the processor is configured to generate the light dose signal in response to image information obtained by a third image modality regarding distribution of a photosensitizer in a body tissue.

6. The photodynamic treatment system according to claim 5, wherein the third image modality is selected from: MR spectroscopy, 19F MRI, nuclear PET imaging, nuclear SPECT imaging, and magnetic particle imaging.

7. The photodynamic treatment system according to claim 5, wherein the second image modality is selected from: FMISO-PET and MRI.

8. The photodynamic treatment system according to claim 1, wherein the processor is configured to determine a planned position of the interventional device in relation to an identified target volume, based on desired position of the fiber ends and the three-dimensional body anatomy image.

9. The photodynamic treatment system according to claim 1, wherein the processor is configured to apply a dynamic light tissue model for calculating a light distribution as a function of temperature dependent local optical properties, photosensitizer concentration, and the concentration of oxygen in body tissue.

10. The photodynamic treatment system according to claim 9, wherein the dynamic light tissue model comprises updating at each time step at least one of:
1) a static light distribution based on actual optical properties, and resulting toxicity based on photosensitizer and the concentration of oxygen,
2) a heat diffusion calculation based on a light diffusion calculation,
3) a damage integral calculation,
4) a change in optical properties due to a change in temperature,
5) a change in photosensitizer concentration, and
6) a change in the concentration of oxygen.

11. The photodynamic treatment system according to claim 1, wherein the optical shape sensing fiber comprises Fiber optic Bragg Gratings to allow the position console to track a three-dimensional shape of the bundle of the plurality of optical fibers, and to determine the actual position and orientation of the fiber ends.

12. The photodynamic treatment system according to claim 1, wherein the interventional device comprises a light intensity sensor.

13. The photodynamic treatment system according to claim 12, wherein the processor is configured to generate the light dose signal in response to information received from the light intensity sensor to adapt light distribution from the interventional device to light applied by an associated additional light source.

14. The photodynamic treatment system of claim 1, wherein the fiber ends are angled to emit the light in the different directions to form angles other than 90° with cross sections of the plurality of optical fibers.

15. The photodynamic treatment system of claim 14, wherein the plurality of optical fibers including the fiber ends are parallel to each other.

16. The photodynamic treatment system of claim 1, wherein the plurality of optical fibers including the fiber ends are parallel to each other.

17. The photodynamic treatment system of claim 1, wherein the optical shape sensing fiber is located at a center of the bundle.

18. A method of photodynamic treatment comprising acts of:
providing in a body an interventional device comprising a bundle of a plurality of optical fibers with distributed fibers ends forming respective light exit ports arranged to emit light in different directions, and an optical shape sensing fiber shared by the plurality of optical fibers for sensing actual position and orientation of the fiber ends actually achieved during use;
determining the actual position and orientation of the fiber ends by applying an optical measurement to the optical shape sensing fiber;
providing a three-dimensional body anatomy image information obtained by a first image modality configured to discriminate between different anatomical tissues inside the body; and
generating individually light outputs to the plurality of optical fibers in response to:
the actual position and orientation of the fiber ends,
knowledge about light emission direction patterns of the light emitted in the different directions from the respective light exit port of the plurality of fiber ends,
the three-dimensional body anatomy image information, and
image information obtained by a second image modality regarding a concentration of oxygen in the body tissue.

19. A photodynamic treatment system comprising:
means for providing in a body an interventional device comprising a bundle of a plurality of optical fibers with distributed fibers ends forming respective light exit ports arranged to emit light in different directions, and an optical shape sensing fiber shared by the plurality of optical fibers for sensing fiber arranged for sensing position and orientation of the fiber ends;
means for determining the position and orientation of the fiber ends by applying an optical measurement to the optical shape sensing fiber;
means for providing a three-dimensional body anatomy image information obtained by a first image modality configured to discriminate between different anatomical tissues inside the body; and
means for generating individually light outputs to the plurality of optical fibers in response to:
the actual position and orientation of the fiber ends,
knowledge about light emission direction patterns of the light emitted in the different directions from the respective light exit port of the plurality of fiber ends,
the three-dimensional body anatomy image information, and
image information obtained by a second image modality regarding a concentration of oxygen in the body tissue.

* * * * *